United States Patent [19]

Goulait et al.

[11] Patent Number: 5,681,306

[45] Date of Patent: Oct. 28, 1997

[54] DISPOSABLE ABSORBENT ARTICLES HAVING IMPROVED TAPE TAB FASTENERS

[75] Inventors: David J. K. Goulait; David W. Cabell; Michael T. Huber; Karl P. Ronn, all of Cincinnati, Ohio

[73] Assignee: The Procter & Gamble Company, Cincinnati, Ohio

[21] Appl. No.: 741,531

[22] Filed: Oct. 31, 1996

Related U.S. Application Data

[63] Continuation of Ser. No. 592,914, Jan. 29, 1996, abandoned, which is a continuation-in-part of Ser. No. 263,115, Jun. 21, 1994, Pat. No. 5,487,809, and Ser. No. 450,773, May 24, 1995, Pat. No. 5,578,152, which is a continuation-in-part of Ser. No. 263,322, Jun. 21, 1994, Pat. No. 5,482,588, and Ser. No. 263,115, Jun. 21, 1994, Pat. No. 5,487,809.

[51] Int. Cl.$^6$ ............................................. A61F 13/15
[52] U.S. Cl. .................................................. 604/390
[58] Field of Search ................................ 604/389, 390, 604/385.1, 385.2, 358

[56] References Cited

U.S. PATENT DOCUMENTS

| | | | |
|---|---|---|---|
| 3,862,634 | 1/1975 | Small | 128/284 |
| 3,893,460 | 7/1975 | Karami | 128/287 |
| 3,897,293 | 7/1975 | Babcock | 156/227 |
| 4,069,077 | 1/1978 | Baumgartner | 156/152 |
| 4,144,887 | 3/1979 | Milnamow | 128/287 |
| 4,389,212 | 6/1983 | Tritsch | 604/389 |
| 4,491,493 | 1/1985 | Eaton | 156/235 |
| 4,531,992 | 7/1985 | Eaton | 156/152 |
| 4,540,415 | 9/1985 | Korpman | 604/389 |
| 4,576,600 | 3/1986 | Joa | 604/390 |
| 5,004,630 | 4/1991 | Polski | 427/208.8 |
| 5,021,111 | 6/1991 | Swenson | 156/264 |
| 5,106,384 | 4/1992 | Polski | 604/390 |
| 5,147,347 | 9/1992 | Huang et al. | 604/389 |
| 5,264,264 | 11/1993 | Shibata et al. | 604/389 |
| 5,288,546 | 2/1994 | Roessler et al. | 604/389 |
| 5,332,607 | 7/1994 | Nakamura et al. | 428/40 |
| 5,342,685 | 8/1994 | Gobran | 428/355 |
| 5,399,177 | 3/1995 | Blaney et al. | 604/389 |
| 5,399,219 | 3/1995 | Roessler et al. | 156/259 |
| 5,482,588 | 1/1996 | Goulait et al. | 156/264 |
| 5,487,809 | 1/1996 | Goulait et al. | 156/259 |

FOREIGN PATENT DOCUMENTS

| | | |
|---|---|---|
| 0 379 850 | 8/1990 | European Pat. Off. . |
| 4-226183 | 8/1992 | Japan . |
| WO 93/22996 | 11/1993 | WIPO . |
| WO 97/04729 | 2/1997 | WIPO . |

*Primary Examiner*—John G. Weiss
*Assistant Examiner*—Ki Yong O
*Attorney, Agent, or Firm*—David M. Weirich; Steven W. Miller; Jacobus C. Rasser

[57] ABSTRACT

Reduced cost absorbent articles comprising improved tape tabs. A preferred embodiment of the present invention comprises a one-piece tape tab joined to each of the ear flaps of the absorbent article. At least a portion of the absorbent article adjacent the end of the tape tab which is permanently joined to the ear flap is mechanically manipulated so as to provide a release surface for storing the fastening end of the tape tab. This embodiment eliminates the need for an added release agent or material, and thus, reduces the overall cost of manufacturing the absorbent article.

13 Claims, 6 Drawing Sheets

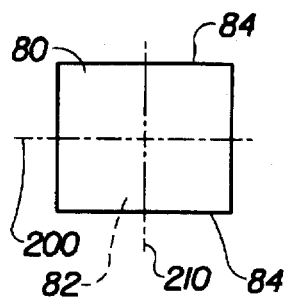 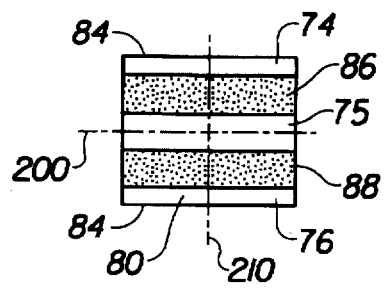 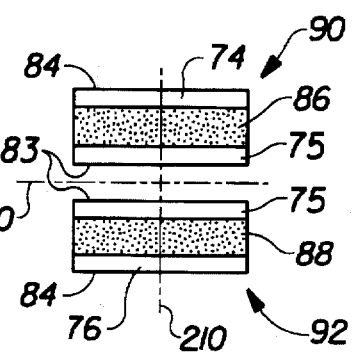
Fig. 11a     Fig. 11b     Fig. 11c
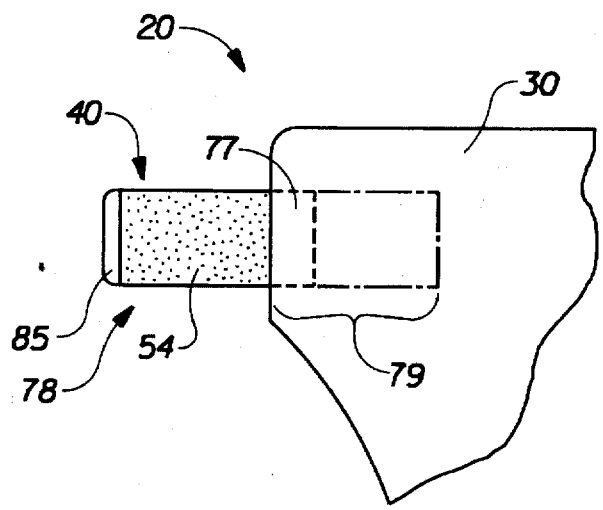
Fig. 12

DISPOSABLE ABSORBENT ARTICLES HAVING IMPROVED TAPE TAB FASTENERS

This application is a continuation of application Ser. No. 08/592,914, filed on Jan. 29, 1996, now abandoned, which is a continuation-in-part of application Ser. No. 08/263,115, filed Jun. 21, 1994, which issued as U.S. Pat. No. 5,487,809 on Jan. 30, 1996; and a continuation-in-part of application Ser. No. 08/450,773, filed May 24, 1995, which has issued as U.S. Pat. No. 5,578,152, which is a continuation-in-part of application Ser. No. 08/263,322, filed Jun. 21, 1994, which has issued as U.S. Pat. No. 5,482,588, and a continuation-in-part of application Ser. No. 08/263,115, filed Jun. 21, 1994, which has issued as U.S. Pat. No. 5,487,809.

FIELD OF THE INVENTION

The present invention relates to disposable absorbent articles comprising improved low-cost tape tab closure members, and more specifically to disposable absorbent articles comprising improved, low cost, one or two-piece tape tab fasteners that can be produced on-line with the articles to which the tape tabs are to be joined.

BACKGROUND OF THE INVENTION

Disposable absorbent articles, such as diapers, training pants, incontinence garments, feminine hygiene garments and the like have become very popular in the market place today. Typically, adhesive tape tabs fasteners are used to secure the absorbent articles about the waist of the wearer. Such fasteners are generally manufactured separately from the articles to which they are attached. For example, it is common for the manufacture of tape tabs to take place in different facilities than the manufacture of the article chassis, and at a different time. Generally, tape tabs are manufactured by applying a release agent to a backing and winding the backing onto a roll. The roll of backing material treated with the release agent is then unwound and coated with fastening adhesive, forming a tape stock. The tape stock is then rewound onto rolls for shipping. Finally, at the place of manufacture of the article chassis, the tape stock is unwound, cut to size, and joined to the articles.

An overriding consideration in the construction of a disposable and/or absorbent article is the cost of manufacturing the article. The present invention provides a reduced cost disposable absorbent articles comprising improved two-piece tape tabs. If desired, the tape tabs can be manufactured concurrently with the absorbent articles to which they will be joined and in the same location, eliminating the need to rewind the tape stock or prepare it for shipping. This also eliminates the need to coat the non-adhesive surface of the tape stock with a release agent, simplifying the process of manufacturing the tape tabs and reducing the overall cost of manufacturing the articles to which the tape tabs are joined.

Alternatively, one-piece tape tabs may be provided having all of the benefits of the two-piece tape tabs. A preferred embodiment of the present invention comprises a one-piece tape tab joined to each of the ear flaps of the article. At least a portion of the article adjacent the end of the tape tab which is permanently joined to the ear flap is mechanically manipulated so as to provide a release surface for releasably storing the fastening end of the tape tab. This embodiment eliminates the need for an added release agent or material, and thus, further reduces the overall cost of manufacturing the absorbent article.

Therefore, it is an object of the present invention to provide a disposable absorbent article comprising a low cost, two-piece tape tab.

It is another object of the present invention to provide a disposable absorbent article comprising a low cost, one-piece tape tab.

It is yet another object of the present invention to provide disposable absorbent article comprising a low cost tape tab having improved processibility and hygiene.

It is still a further object of the present invention to provide an absorbent article comprising mechanically manipulated regions that act as release surfaces for the fastening ends of the tape tabs.

These and other objectives of the present invention will be more readily apparent when considered in reference to the following description and when taken in conjunction with the accompanying drawings.

SUMMARY OF THE INVENTION

The present invention provides a disposable absorbent article comprising improved, low-cost tape tabs which may be manufactured on-line and concurrently with the chassis of the absorbent article to which the tape tabs will be attached. The first step in manufacturing the tape tabs is to provide a backing substrate upon which the adhesives of the tape tab can be applied. Once the backing is provided, a fastening adhesive is preferably applied to regions of one side of the backing substrate. (The fastening adhesive preferably functions as the adhesive used to fasten an element of the absorbent article, such as a front waist region, to another element of the absorbent article, such as a rear waist region.) The backing substrate is then slit in a direction parallel to the machine direction and the release surface of a release substrate is placed in contact with the fastening adhesive, forming a laminate comprising the backing substrate and the release substrate. The release substrate preferably covers the entire surface of the backing substrate upon which fastening adhesive has been applied. However, in a preferred embodiment, at least a portion of the backing substrate extends outwardly in a direction parallel to the cross machine direction beyond the longitudinal edges of the release substrate. The surface of the laminate, including the surface of the release substrate that is not in contact with the fastening adhesive, and any of the backing substrate not covered by the release substrate is then coated with a construction adhesive. (The construction adhesive is used to join the tape tabs to the absorbent article.) After the construction adhesive is applied to the surface of the laminate, the laminate is slit in a direction parallel to the machine direction and either rewound for shipping or storage, or fed to a taper unit that is integrated into the absorbent article manufacturing line. The taper unit cuts individual tape tabs and applies them to the absorbent article chassis.

An alternative embodiment of the present invention provides a one-piece tape tab manufactured by providing a backing substrate having a fastening adhesive applied to one surface. However, rather than utilizing a separate release substrate to form a release surface for the fastening adhesive of the tape tabs, the backing substrate comprises an integral release surface to which the fastening adhesive of the tape tab may be releasably fastened. Another one-piece tape tab may be provided having a fixed end permanently bonded to at least a portion of the absorbent article. The permanent bond preferably not only joins the fixed end of the tape tab to the absorbent article, but also forms a region on the outwardly facing surface of the fixed end of the tape tab that may act as a release surface for the fastening adhesive. To reduce the mount of backing substrate needed, and to provide a larger release surface for the releasable end of the tape tab, an area of the absorbent article adjacent to the fixed end of the tape tab may be subjected to mechanical manipulation. The region of mechanical manipulation may form a region on the surface of the absorbent article that acts a release surface for the fastening adhesive disposed on the releasable end of each tape tab.

BRIEF DESCRIPTION OF THE DRAWINGS

While the specification concludes with claims particularly pointing out and distinctly claiming the subject matter which is regarded as the present invention, it is believed that the invention will be better understood from the following description which is taken in conjunction with the accompanying drawings in which like components have similar designations.

FIGS. 11a–11c represent a plan view of the process for on-line manufacturing one-piece tape tabs for use with absorbent articles.

FIG. 12 is a plan view of a portion of an absorbent article comprising one preferred one-piece tape tab.

DETAILED DESCRIPTION OF THE INVENTION

The present invention generally relates to disposable absorbent articles comprising improved tape tab fasteners. However, it should be noted that the article to which the tape tab fasteners are joined can be disposable and not an absorbent article as described herein, or can be reuseable absorbent articles, and thus, not disposable as defined below. As used herein, the term "absorbent article" refers to devices which absorb and contain body exudates, and more specifically, refers to devices which are placed against the skin of a wearer to absorb and contain the various exudates discharged from the body. The term "disposable" is used herein to describe absorbent articles which are not intended to be laundered or otherwise restored or reused as an absorbent article after a single use (i.e. they are intended to be discarded, and preferably, recycled, composted or otherwise disposed of in an environmentally compatible manner). A "unitary" absorbent article refers to an absorbent article which is formed from separate parts united together to form a coordinated entity so that they do not require separate manipulative parts like a separate holder and liner. As used herein, the term "diaper" refers to an absorbent article generally worn by infants and incontinent persons that is generally worn about the lower torso of the wearer. It should be understood, however, that the present invention is also applicable to other absorbent articles such as incontinence briefs, diaper holders, feminine hygiene garments, training pants, panties, underwear and the like. One preferred embodiment of the present invention is the disposable absorbent article shown in FIG. 1.

Figure 1:
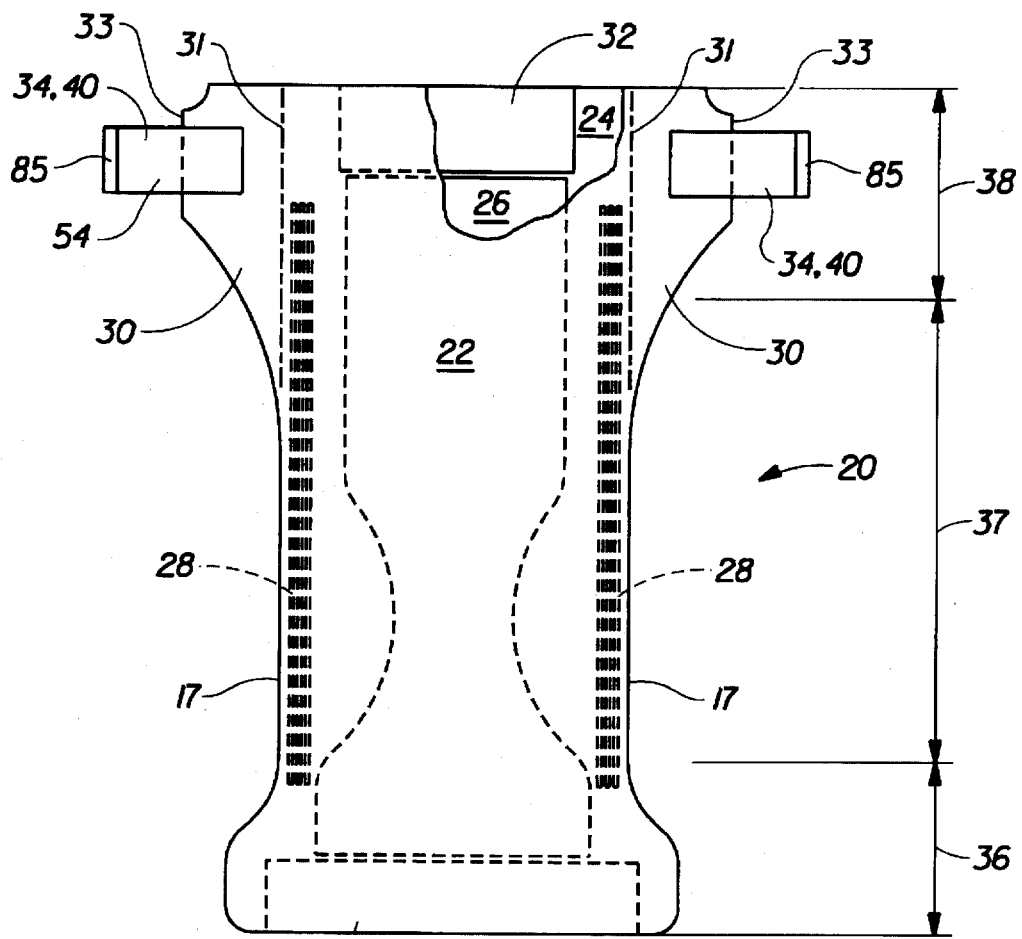
FIG. 1 is a plan view of an absorbent article comprising one embodiment of the low-cost tape tab of the present invention.

With reference to FIG. 1, an absorbent article, such as diaper 20, generally comprising a chassis 15 having a pair of longitudinal edges 17, a liquid permeable topsheet 22, a liquid impermeable backsheet 24, and an absorbent core 26 between the topsheet 22 and the backsheet 24. The diaper 20 preferably further comprises a front waist region 36, a rear waist region 38, a crotch region 37 disposed between the front waist region 36 and the rear waist region 38, elasticized leg cuffs 28, ear flaps 30, an elastic waist feature 32 and a fastening system 34 comprising at least one tape tab 40. (It should be understood that the front waist regions 36 and the rear waist region 38 are defined as such merely as one preferred embodiment. However, embodiments are contemplated wherein what is herein described as the front waist region could be the rear waist regions, and vice versa.) An example of a preferred absorbent article to which the tape tabs of the present invention may be joined is more fully and completely described in U.S. Pat. No. 5,151,092 entitled "Absorbent Article With Dynamic Elastic Waist Feature Having A Predisposed Resilient Flexural Hinge", issued to Buell et al. on Sep. 29, 1992 which is hereby incorporated by reference herein.

In one preferred embodiment, an ear flap 30 extends laterally outwardly from each of the longitudinal edges 17 of the chassis 15, preferably in at least the rear waist region 38. The ear flaps 30 may be integral with an element or elements of the chassis 15 (i.e. extensions of the topsheet 22, the backsheet 24, or both), or may be separate members joined to the chassis 15. Further, the ear flaps 30 may be single or multiple components which may include extensible or non-extensible materials. As shown in FIG. 1, the tape tabs 40 are preferably disposed adjacent the distal edges 33 of the ear flaps 30. The distal edges 33 of the ear flaps 30 are disposed laterally outwardly from the proximal edges 31 when the diaper is in a flat-out, uncontracted state. (In FIG. 1, the ear flaps 30 are shown to be integral members of the diaper 20, thus, the proximal edges 31 of the ear flaps are shown by the imaginary lines designated 31.) In embodiments where the ear flaps 30 are separate members, it is preferred that at least a portion of the proximal edge 31 of each ear flap 30 be joined adjacent one of the opposing longitudinal edges 17 of the chassis 15. The ear flaps 30 may he joined by any means known in the art, including adhesives, heat, pressure, ultrasonics or any combination thereof. Further, the ear flaps 30 may be disposed on the topsheet 22, the backsheet 24 or between the topsheet 22 and the backsheet 24, and may be joined to the topsheet 22, the backsheet 24 or both.

Figure 8:
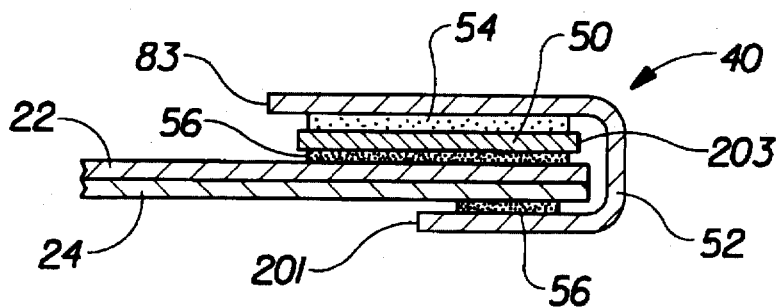
FIG. 8 is cross-sectional view of a preferred embodiment of a two-piece tape tab.
Figure 9:
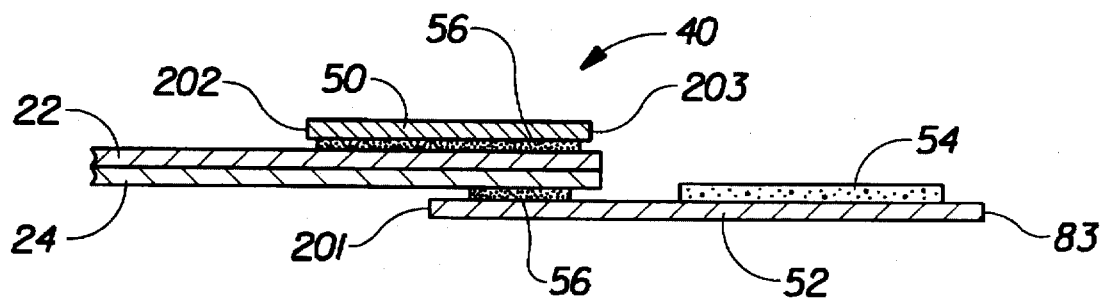
FIG. 9 is cross-sectional view of a preferred embodiment of an alternative two-piece tape tab.

One preferred tape tab is shown in FIGS. 8 and 9. The tape tab 40 comprises a backing substrate 52 comprising at least one construction adhesive 56 and one fastening adhesive 54. (However, it should be noted that the construction adhesive 56 may comprise the fastening adhesive.) The construction adhesive 56 is attached to the backsheet 24 and is separated from the fastening adhesive 54 preferably a distance greater than or equal to about 0.5 mm. The construction adhesive 56 is preferably spaced inwardly from the backing substrate 52 edge 201 by a distance greater than or equal to about 0.5 mm. The fastening adhesive 54 is preferably spaced inwardly from the backing substrate edge 83 by a distance of greater than about 0.5 mm. A release surface 50 is preferably attached to the topsheet 22 by a permanent adhesive 56 which ends at a distance greater than or equal to about 0.5 mm from edge 203 of the release substrate 50. In another preferred execution the permanent adhesive 56 also ends at a distance greater than or equal to about 0.5 mm from edge 202 of the release substrate. (As used herein, the terms "permanent adhesive" refers to an adhesive used to bond one element with another element, wherein the bond between the elements is relatively strong such that the elements will not generally become unjoined during normal use of the product.)

Figure 10:
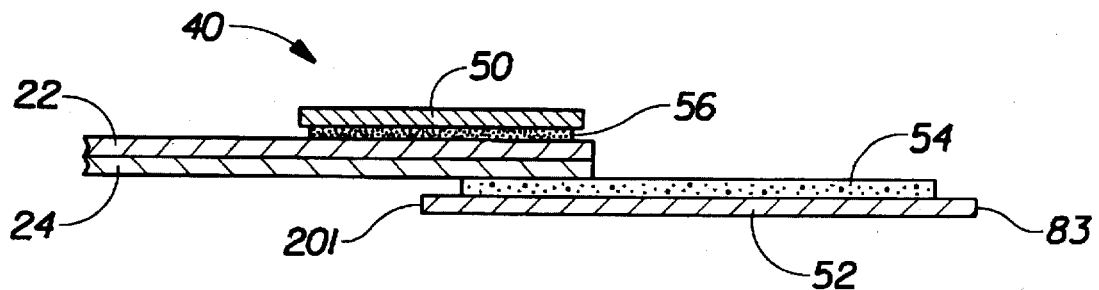
FIG. 10 is cross-sectional view of an alternative preferred embodiment of an alternative two-piece tape tab.

An alternative preferred adhesive tape tab 40 is shown in FIG. 10. The tape tab 40 comprises a backing substrate 52 comprising a single adhesive 54. The adhesive 54 serves to join the backing substrate 52 to the backsheet 24 as well as provide a surface which may be used for fastening. The adhesive 54 is preferably inwardly positioned from edges 83 and 201 of the backing substrate 52 by a distance greater than or equal to about 0.5 mm. The release substrate 50 is preferably joined to the topsheet 22 with a construction adhesive as described with regard to the tape tab of FIGS. 8 and 9.

Overall method of on-line manufacture of tape tabs

The tape tabs 40 of the present invention may be made by first providing a backing substrate upon which the adhesives of the tape tab 40 can be applied. A fastening adhesive is applied to regions of one side of the backing substrate. The fastening adhesive may comprise any adhesive suitable for joining the fastening end of the tape tab to another element of the absorbent article, such as the front waist region 36. Examples of suitable fastening adhesives may comprise pressure-sensitive adhesives, cohesives and the like. The backing substrate is then preferably slit in a direction parallel to the machine direction and a release substrate is placed in contact with the fastening adhesive, forming a laminate comprising the backing substrate, the fastening adhesive and the release substrate. The surface of the laminate, including the surface of the release substrate, as well as any portion of the backing substrate not covered by the release substrate is then coated with a construction adhesive which joins the tape tabs to the absorbent article. After the construction adhesive is applied to the surface of the laminate, the laminate is preferably slit in a direction parallel to the machine direction and fed to a taper unit that is integrated into the absorbent article manufacturing line. The taper unit cuts individual tape tabs 40 from the laminate and joins the tape tabs 40 to the absorbent articles. This process is generally illustrated in FIGS. 2 and 3.

Figure 2:
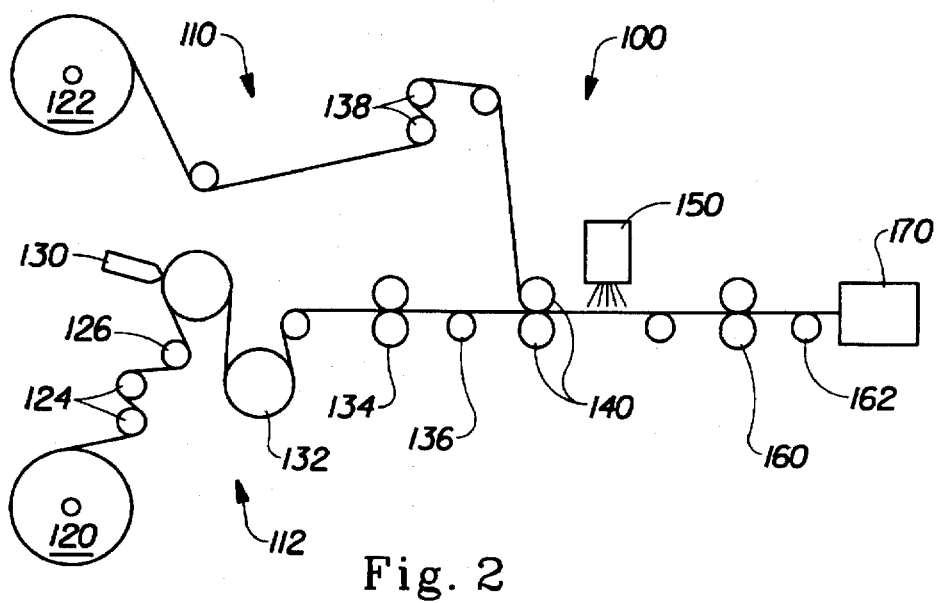
FIG. 2 is a representative side view of the process for on-line manufacturing tape tabs for use with the absorbent articles of the present invention.

The tape tabs 40 may be produced on the apparatus 100, as shown in FIG. 2. The apparatus 100 comprises two separate process modules, process module 110 for providing a release substrate 50; and process module 112 for providing a backing substrate (or "backing") 52, applying a fastening adhesive 54 to the backing 52 and slitting the backing 52 prior to contacting the release substrate 50 to the fastening adhesive 54 disposed on the backing 52. In a preferred embodiment, the apparatus 100 is integrated into a disposable absorbent article manufacturing line such that the tape tabs 40 are manufactured "on-line". (As used herein, the term "integrated" means interconnected process modules that operate concurrently to produce finished products from source materials. The term "on-line" is used to refer to the process of manufacturing the tape tabs 40 of the present invention on an apparatus that is integrated with the manufacturing line that produces the absorbent articles to which the tape tabs will be joined.)

The backing substrate

Examining process module 112 in greater detail, a backing substrate 52 is provided and taken from the unwind roll 120. The backing substrate 52 may comprise any material to which a fastening adhesive and a construction adhesive, such as a hot melt adhesive, may be applied. Some nonlimiting examples of suitable backing substrates include films, laminates, woven and nonwoven webs, foams, and the like. In a preferred embodiment, the backing substrate 52 comprises a cellulose, polyolefin or polyester film ranging in thickness from about 2.5 mils to about 5.0 mils in thickness, more preferably about 4 mils in thickness. A polyolefin film that has been found to be particularly suitable for the backing substrate is the polypropylene film manufactured by the Exxon Chemical Company of Lake Zurich, Ill., under the trade name EX-377. A cellulose film that has been found to be suitable is manufactured by the Kimberly-Clark Corporation of Dallas, Tex. under the trade name C-49490.

As shown in FIG. 2, the backing substrate 52 is taken from the unwind roll 120 and passes through the S-wrap tensioning rolls 124 to provide proper tensioning and to prevent puckering or bunching of the backing 52. If necessary, a tracking system (not shown) as is commonly utilized and known in the art, may be employed in the process module 112 to optimally track and adjust the backing substrate 52 into the S-wrap tensioning rolls 124. A tracking system manufactured by the Fife Corporation of Oklahoma City, Okla., and sold as Model Op6 LRA may be suitable.

Guide roll 126 guides the backing 52 into position adjacent the adhesive slot coater 130 for application of the fastening adhesive 54. The adhesive slot coater 130 may be any adhesive slot coater as is known in the art. Similarly, the fastening adhesive 54 may be any fastening adhesive as is known in the art, including, but not limited to fastening adhesives, cohesives, solvent based adhesives or water based adhesives. Some examples of preferred fastening adhesives include the pressure-sensitive adhesives HL-1414 and HL-1350 manufactured by the H. B. Fuller Company of St. Paul, Minn., and H-2153 manufactured by the Findley Adhesive Corporation of Wauwatosa, Wis. The adhesive slot coater 130 preferably applies the fastening adhesive 54 to the backing 52 in a heated, liquid state. The construction adhesive 56 may be applied in any pattern as is known in the art, including but not limited to lines, dots, spirals or a generally continuous layer of adhesive. The slot coater 130 preferably applies the adhesive 54 to the backing 52 such that adhesive free gaps 74, 75, and 76 are present. These gaps are preferably greater than or equal to about 0.5 mm to aid in processibility (i.e., slitting, if required) and process hygiene. After the fastening adhesive 54 is applied, the backing 52 is preferably directed to a chill roll 132 such that the fastening adhesive 54 is cooled and permitted to solidify on the surface of the backing 52.

Once the fastening adhesive 54 has been applied, and preferably cooled, the backing 52 is preferably directed to a shear slitting apparatus 134 that slits the backing 52 in a direction parallel to the machine direction. The slitting operation preferably slits the backing 52 within the adhesive free area 75. (It should be noted, however, in less preferred embodiments, the backing 52 is not slit and separated. In such embodiments, a single piece of tape tab stock 70 results rather than the multiple segments as described more fully below with regard to the preferred embodiments.) The backing 52 is then separated laterally at the slit. (As used herein, the term "laterally" is defined as the direction perpendicular to the machine direction, or parallel to the cross machine direction.) The backing 52 may be separated by any means as are known in the art, including but not limited to any web spreader 136 as is known in the art.

The release substrate

The backing 52 comprising the fastening adhesive 54 is directed to a nip between the combining rolls 140 where the surface of the backing 52 comprising the fastening adhesive 54 is placed in contact with the release surface of a release substrate 50. The release substrate 50 generally comprises a base material and a release agent disposed on at least one surface of the base material. However, release substrates are available wherein the base material itself acts as a release agent, and thus, no other release agent is needed. The release agent may be applied to the base material "on-line", or at a time and/or location remote from the rest of the process described herein. The base material of the release substrate 50 may be any material as is known in the art, including, but not limited to films, laminates, woven and nonwoven webs, foams, and the like. Examples of suitable base materials for the release substrates of the present invention comprise cellulose materials or polypropylene films, ranging in thickness from 1.0 to 5.0 mils. One preferred base material for the release substrate 50 is the polypropylene film EX-399 manufactured by the Exxon Chemical Company of Lake Zurich, Ill. Another preferred base material for the release substrate 50 is the cellulose film 1224212 manufactured by the Rhinelander Paper Company of Rhinelander, Wis. The release agent may be any release agent as is known in the art that will act as a release agent for the particular fastening adhesive 54 utilized. An example of a suitable release agent that works well with many different base materials and fastening adhesives is silicone. The Goldschmidt Company of Essen, West Germany manufactures silicone formulas that can be used as release agents under the trade names RC711 or RC726. (In preferred embodiments, the release agent comprises a mixture of the RC711 and RC726 silicone formulas.)

As shown in FIG. 2, the release substrate 50 is taken from the unwind roll 122 and passes through the S-wrap tensioning rolls 138 to provide proper tensioning and to prevent puckering or bunching of the release substrate 50. If necessary, a tracking system (not shown) as is commonly utilized and known in the art, may be employed in the process module 110 to optimally track and adjust the release substrate 50 into the S-wrap tensioning rolls. As with the process module 112, a tracking system manufactured by the Fife Corporation of Oklahoma City, Okla., and sold as Model Op6 LRA may be suitable to ensure proper tracking of the release substrate 50 in the process module 110.

Joining the backing substrate with the release substrate

The surface of the backing substrate 52 comprising the fastening adhesive 54 is contacted with the surface of the release substrate 50 comprising the release agent as the substrates pass through the nip between the combining rolls 140. The backing substrate 52 and the release substrate 50 become releasably joined together, forming laminate 60. The laminate 60 is directed to pass adjacent an adhesive spray nozzle 150 where a construction adhesive 56 is applied to the surface of the release substrate 50, forming a tape tab stock 70. The spray nozzle 150 may be any adhesive spray nozzle known in the art, including, but not limited to a J&M meltblown nozzle available from J&M Laboratories, Inc., of Dawsonville, Ga. or a Nordson spiral nozzle available from the Nordson Corporation of Norcross, Ga. The construction adhesive 56 may comprise any adhesive or combination of adhesives known in the art, including, but not limited to, pressure-sensitive adhesives, cohesives, solvent based adhesives or water based adhesives. Preferably, however, the construction adhesive 56 is a permanent hot melt adhesive. One such adhesive is the hot melt adhesive HL-1358, manufactured by the H. B. Fuller Company of St. Paul, Minn. The construction adhesive 56 may be applied in any pattern as is known in the art, including but not limited to lines, dots, spirals or a generally continuous layer of adhesive. In one preferred embodiment, the width of adhesive 56 is applied such that there is an adhesive free area of greater than or equal to about 0.5 mm from the side edge 100 of the release substrate 50. It is also preferred to have an adhesive free area 101 parallel to the longitudinal centerline L of greater than or equal to about 0.5 mm. This aids processibility and hygiene in embodiments wherein the tape tab stock 70 is slit along the longitudinal centerline L.

After the construction adhesive 56 is applied to the tape tab stock 70, the tape tab stock 70 is preferably directed to a second shear slitter 160 where the tape tab stock 70 is slit in a direction parallel to machine direction. The tape tab stock 70 is then separated at the slit by a tape tab stock spreader 162 and fed directly into a standard taper unit 170 as is commonly known in the art. One suitable taper unit, as supplied by Curt G. Joa, Inc., of Sheboygan Falls, Wis., feeds the tape tab stock 70 to a vacuum anvil roll where the tape tab stock 70 is cut into individual tape tabs 40, spaced apart (slipped) and joined to the absorbent article.

Alternatively, the tape tab stock 70 may be rewound for storage or shipment and later fed into a taper unit on an absorbent article manufacturing line. If rewinding of the tape tab stock 70 is desired, it is preferred that the construction adhesive 56 have the ability to lose its adhesive properties during the period in which the tape tab stock 70 is wound and yet be able to reactivated upon demand at a later time. (As used herein, the term "reactivated" refers to the ability of an adhesive that has lost its adhesive properties to regain its adhesive properties at a later time.) Some nonlimiting examples of adhesives that have the ability to lose their adhesive properties and to be reactivated at a later time include hot melt adhesives, water activated adhesives, radiation activated adhesives and ultra-violet light activated adhesives.

Preferred Tape Tab Embodiments a. Two-piece tape tab

Figure 3A:
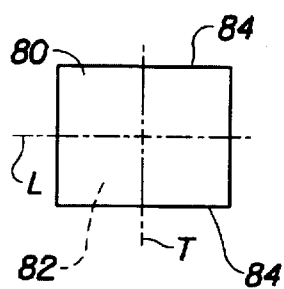
FIGS. 3a–3f represent a plan view of one process for on-line manufacturing tape tabs for use with the absorbent articles of the present invention.
Figure 3B:
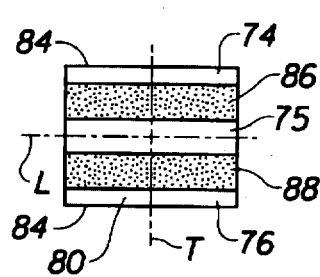
Figure 3C:
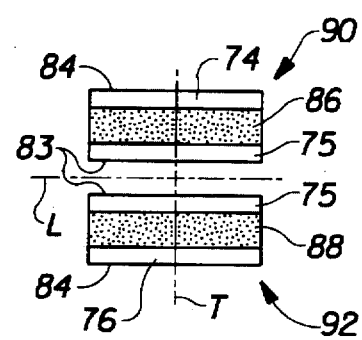

One preferred method for manufacturing a preferred two-piece tape tab is depicted in FIGS. 3a–3f. As shown in FIG. 3a, a backing substrate 52, as described above, is provided having a longitudinal centerline L and a transverse centerline T perpendicular to the longitudinal centerline L. (As used herein, the term "longitudinal centerline" refers to an imaginary line that runs parallel to the machine direction. The "transverse centerline runs perpendicular to the machine direction and parallel to the cross machine direction.) The backing substrate 52 further comprises a first surface 80, a second surface 82 opposed to the first surface 80, and a pair of outer longitudinal edges 84. (As shown in FIG. 3c, the backing substrate 52 further comprises a pair of inner longitudinal edges 83 once the backing substrate has been slit.)

FIG. 3b shows a plan view of the backing substrate 52 after it has passed the slot coater 130, having the fastening adhesive 54 applied to the first surface 80. In a preferred embodiment, the fastening adhesive 54 is not applied to the entire first surface 80 of the backing substrate 52. Rather, it is preferred that the fastening adhesive 54 be applied continuously to the backing substrate 52 in zones, preferably at least a first zone 86 and a second zone 88. (As used herein, the term "continuously" means a generally unbroken pattern.) The first zone 86 and the second zone 88 are preferably disposed transversely inwardly from the outer longitudinal edges 84 of the backing substrate 52. (As used herein, the term "transversely inwardly" means toward the longitudinal centerline. The term "transversely outwardly" means away from the longitudinal centerline.) The area between the outer longitudinal edges 84 of the backing substrate 52 and the zones 86 and 88 of fastening adhesive 54 creates fixed regions 74 and 76. These fixed regions 74 and 76 are preferably greater than or equal to about 0.5 mm, to aid in processibility and cleanliness of the process.

Figure 5:
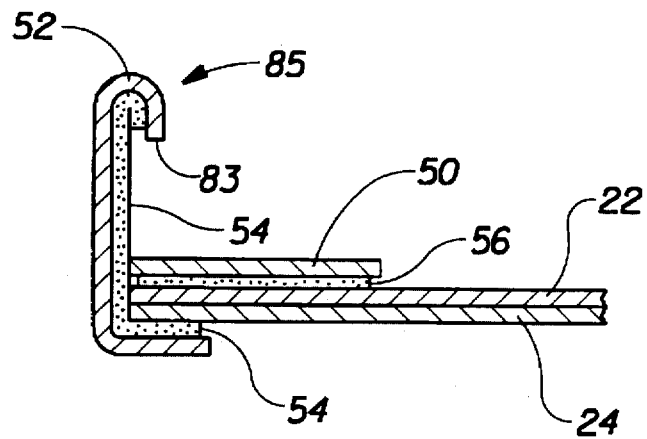
FIG. 5 is cross-sectional view of a two-piece tape tab.
Figure 7:
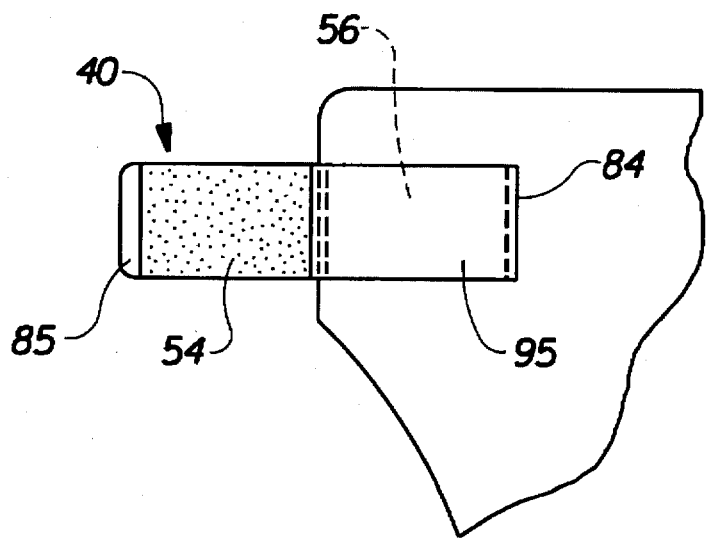
FIG. 7 is a plan view of a portion of an absorbent article comprising a one-piece tape tab.

The first zone 86 and the second zone 88 are also preferably transversely separated about the longitudinal centerline L. This leaves a nonadhesive area 75, preferably greater than or equal to about 0.5 mm, between the first zone 86 and the second zone 88 that can be used as a release tab 85. The non-adhesive area 75, also aids in processibility by aiding the slitting operation 134. The release tab 85, as shown in FIGS. 5 and 7, provides the user with a portion of the backing substrate 52 which is free of fastening adhesive 54 and preferably not adhered to the release substrate or any other element of the diaper 20. Thus, the user may grasp the release tab 85 and more easily open the tape tab 40. (As used herein, the term "open the tape tab" refers to separating the fastening adhesive 54 disposed on the tape tab 40 from the release substrate 50 or any other surface to which the fastening adhesive 54 may be adhered.) However, if the first zone 86 and the second zone 88 are not transversely separated about the longitudinal centerline L, alternative methods of providing a release tab 85 are available. The methods include, but are not limited to, folding a portion of the backing substrate 52 adjacent the inner longitudinal edges 83 onto the fastening adhesive 54 disposed on the backing substrate 52 (shown in FIG. 5), or coating the backing substrate 52 adjacent the inner longitudinal edges 83 with a release agent or any other material that will prevent the fastening adhesive 54 in the area adjacent the inner longitudinal edges 83 from adhering to the release substrate 50 or any other elements of the diaper 20.

As shown in FIG. 3c, the backing substrate 52 is preferably slit along the longitudinal centerline L, forming two backing substrate segments, 90 and 92. (Embodiments are contemplated, however, wherein more than two zones of fastening adhesive 54 are applied to the backing substrate 52 and wherein the backing substrate 52 is slit and separated into more than two backing segments.) The backing substrate segments, 90 and 92, are preferably separated transversely before they are brought into contact with the release substrate 50 (shown in FIG. 3d).

Figure 3D:
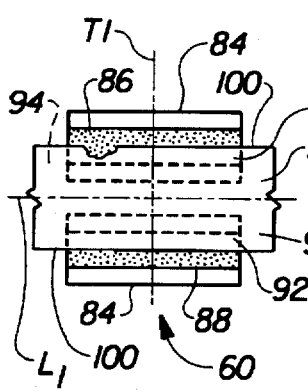

The release substrate 50 has a release surface 94 and an adhesive surface 96 opposed the release surface 94. The release surface 94 is preferably comprises a release agent as described above, and is placed in contact with the fastening adhesive 54 disposed on the first surface 80 of backing substrate segments 90 and 92. In a preferred embodiment, as shown in FIG. 3d, the release substrate 50 at least partially covers both the first zone 86 and the second zone 88 of fastening adhesive 54; the first zone 86 being disposed on segment 90 and the second zone 88 being disposed on the segment 92 of the separated backing substrate 52.

Figure 3E:
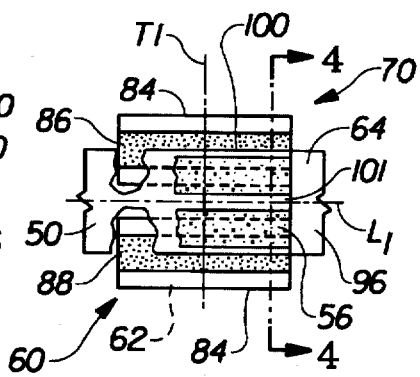

Once the release surface 94 of the release substrate 50 contacts the zones 90 and 92 of fastening adhesive 54, the segments 90 and 92 of the backing substrate 52 become releasably joined to the release substrate 50, forming a laminate 60. The laminate 60, as shown in FIG. 3e, has an outer surface 62, an adhesive surface 64, a longitudinal centerline L1 and a transverse centerline T1. The adhesive surface 64 of the laminate 60 comprises the adhesive surface 96 of the release substrate 50. As as shown in FIG. 2, the laminate 60 is preferably passed adjacent a spray nozzle 150 that applies a construction adhesive 56 to the adhesive surface of the release substrate 50. The construction adhesive 56 may be applied to the entire adhesive surface 96 of the release substrate 50. In a preferred embodiment, as shown in FIG. 3e, however, the construction adhesive 56 is applied laterally inwardly from the side edges 100 of the release substrate 50 up to about 0.5 mm to ensure the cleanliness of the process. (As noted above, the adhesive may be applied continuously or in any pattern.) In another preferred embodiment, the construction adhesive applied in transversely separated zones such that an adhesive free area 101 is present preferably parallel to and juxtaposed or coincident with the longitudinal centerline L1. The adhesive free area 101 is preferably greater than or equal to about 0.5 mm to aid in the slitting operation that takes place at shear slitter 160. The construction adhesive 56 preferably comprises a permanent, hot melt adhesive as described above.

Figure 3F:
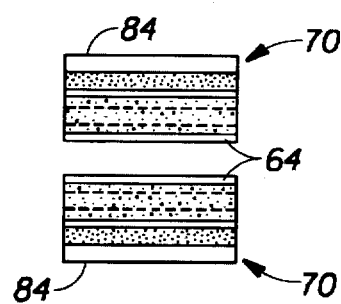
Figure 4:
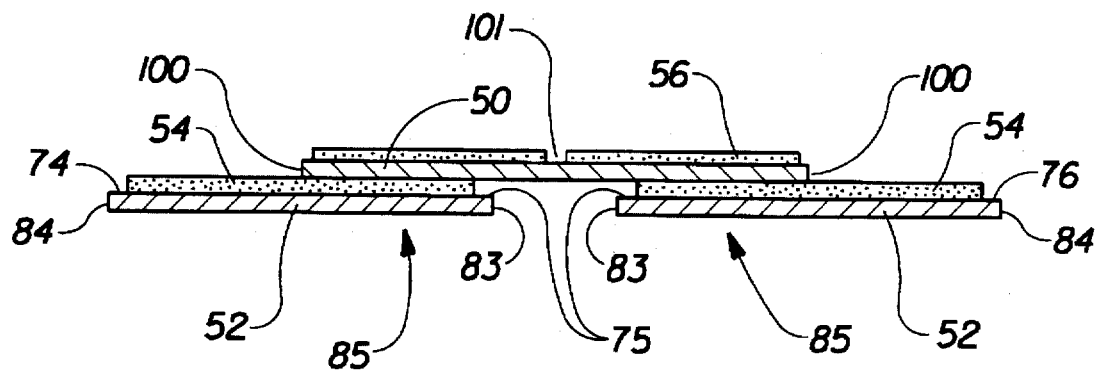
FIG. 4 is a cross-sectional view of the laminate shown in FIG. 3e.

After the construction adhesive 56 is applied to the adhesive surface 96 of the release substrate 50, the laminate 60 is preferably slit along its longitudinal centerline L1 and separated to form tape tab stock 70, as shown in FIG. 3f. The tape tab stock 70 has a longitudinal centerline L2, a transverse centerline T2 perpendicular to the longitudinal centerline L2, an adhesive surface 102 and a non-adhesive surface 104. The tape tab stock 70 is preferably fed directly into the taper unit 170 that can be integrated into the absorbent article manufacturing line. The taper unit 170 cuts the tape tab stock 70 in a direction parallel to the transverse centerline T2 to form the individual tape tabs 40. The taper unit 170 then joins the adhesive surface 102 of the tape tabs 40 to individual absorbent articles manufactured concurrently with the tape tabs 40.

b. One-piece tape tab

Figure 6:
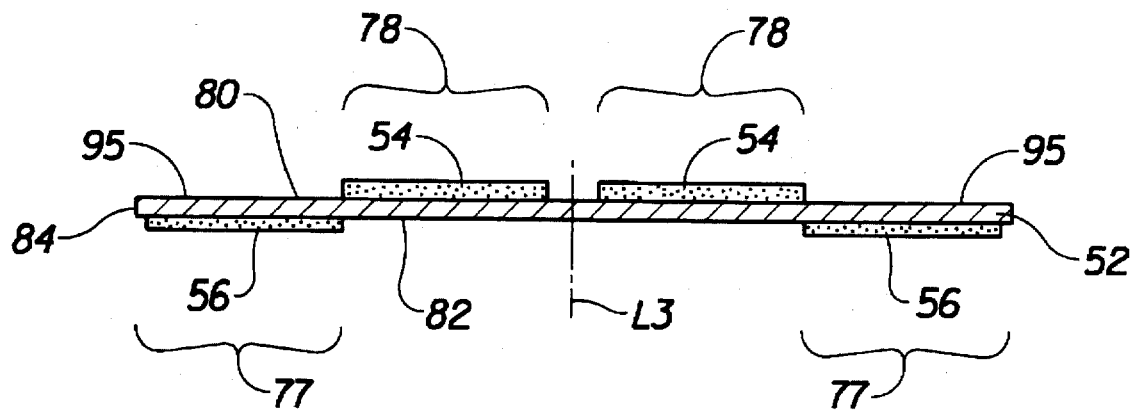
FIG. 6 is a cross-sectional view of the laminate that forms one embodiment of the one-piece tape tab of the present invention.

A preferred one-piece tape tab is shown in FIG. 7. The tape tab 40 may be joined to the absorbent article with a permanent construction adhesive as described above with regard to the two-piece tape tab. In this embodiment, the steps described above relating to the preparation of a backing substrate 52 comprising zones 86 and 88 of fastening adhesive 54 are followed. As shown in FIG. 6, the fastening adhesive 54 is preferably applied in zones that are transversely separated about the longitudinal centerline L3 such that the width between the zones is greater than or equal to about 0.5 mm. However, before the backing substrate 52 is slit and separated, a construction adhesive 56 is applied to the second surface 82 of the backing substrate 52. Preferably, the construction adhesive 56 is applied continuously to the backing substrate 52 in zones, rather than to the entire second surface 82 of the backing substrate 52. The zones of construction adhesive 56 are preferably transversely separated about the longitudinal centerline L3. Further, as shown in FIG. 6, the zones of construction adhesive 56 are preferably disposed transversely inwardly or transversely outwardly from the zones of fastening adhesive 54 and preferably disposed inwardly from edge 84 greater than or equal to about 0.5 mm. This ensures that at least a portion of the backing substrate 52 comprising the fastening adhesive 54 can be folded over the first surface 80 of the backing substrate 52 to form a tape tab 40 once the backing substrate 52 is slit into segments.

The backing substrate 52 is preferably slit along the longitudinal centerline L3 and separated, forming at least two backing substrate segments as described above. These backing substrate segments are fed directly into a taper unit 170 which cuts the backing substrate segments into individual tape tabs 40. Each individual tape tab has a fixed end 77 and a releasable end 78. The releasable end 78 preferably comprises the fastening adhesive 54 applied to the substrate backing 52. (In especially preferred embodiments, the releasable end comprises a release tab 85 as described above.) The fixed end 77 preferably comprises the construction adhesive 56 disposed on the second surface 82 and a release surface 95. The release surface 95 may comprise any release agent known in the art, including but not limited to, silicone, wax, or day; or the release surface 95 may be formed by impregnating predetermined portions of the backing substrate 52 with a release agent, or by embossing or bonding the backing substrate 52 such that a release surface 95 is formed. Alternatively, a backing substrate 52 may be chosen that comprises areas of differing molecular structures, such as laminates or coextruded films, wherein at least a portion of the first surface 80 of the backing substrate 52 acts as a release surface 95.

Finally, the tape tab stock 70 is fed into a standard taper unit as is commonly known in the art. One such unit, as supplied by Curt G. Joa, Inc., of Sheboygan Falls, Wis., feeds the tape tab stock 70 to an anvil roll where the tape tab stock 70 is cut into individual tape tabs 40. The individual tape tabs 40 are then slipped (spaced) and the fixed end 77 of each tape tab 40 is joined to the absorbent article by means of the construction adhesive 56 disposed on the second surface 82 of the backing substrate 52.

Another preferred one-piece tape tab is shown in FIG. 12. As described above, the tape tabs 40 may be made by first providing a backing substrate upon which the fastening adhesive of the tape tab 40 can be applied. FIG. 11 shows the backing substrate 52 having a longitudinal centerline 200 and a transverse centerline 210 perpendicular to the longitudinal centerline 200. The backing substrate 52 further comprises a first surface 80, a second surface 82 opposed to the first surface 80, and a pair of outer longitudinal edges 84. (As shown in FIG. 11, the backing substrate 52 further comprises a pair of inner longitudinal edges 83 once the backing substrate has been slit.)

FIG. 11 shows a plan view of the backing substrate 52 after the fastening adhesive 54 has been applied to the first surface 80. In a preferred embodiment, the fastening adhesive 54 is not applied to the entire first surface 80 of the backing substrate 52. Rather, it is preferred that the fastening adhesive 54 be applied continuously to the backing substrate 52 in zones, preferably at least a first zone 86 and a second zone 88. The area between the outer longitudinal edges 84 of the backing substrate 52 and the zones 86 and 88 of fastening adhesive 54 creates fixed regions 74 and 76. (These fixed regions 74 and 76 may be the portions of the tape tabs 40 that become permanently fixed to the absorbent article.)

The first zone 86 and the second zone 88 are also preferably transversely separated about the longitudinal centerline 200. This leaves a non-adhesive area 75 between the first zone 86 and the second zone 88 that may be utilized as a release tab 85. The release tab 85, as shown in FIG. 12 provides the user with a portion of the backing substrate 52 which is free of fastening adhesive 54 and preferably not adhered to the release substrate or any other element of the diaper 20. Thus, the user may grasp the release tab 85 and more easily open the tape tab 40. However, if the first zone 86 and the second zone 88 are not transversely separated about the longitudinal centerline 200, alternative methods of providing a release tab 85 are available. The methods include, but are not limited to, folding a portion of the backing substrate 52 adjacent the inner longitudinal edges 83 onto the fastening adhesive 54 disposed on the backing substrate 52 or coating the backing substrate 52 adjacent the inner longitudinal edges 83 with a release agent or material that will prevent the fastening adhesive 54 in the area adjacent the inner longitudinal edges 83 from adhering to the release surface 79 or any other elements of the diaper 20. (The release surface 79 is described in greater detail below.)

As shown in FIG. 11, the backing substrate 52 is preferably slit along the longitudinal centerline 200, forming at least two backing substrate segments, 90 and 92. (Embodiments are contemplated, however, wherein more than two zones of fastening adhesive 54 are applied to the backing substrate and wherein the backing substrate is slit and divided into more than two backing substrate segments.) The backing substrate segments, 90 and 92, are preferably separated transversely before they are directed to a taper unit. A taper unit cuts the backing substrate segments 90 and 92 into individual tape tabs 40. Each individual tape tab 40 has a fixed end 77 and a releasable end 78 (shown in FIG. 12). The releasable end 78 preferably comprises the fastening adhesive 54 applied to the substrate backing 52. The fixed end 77 preferably comprises one of the fixed regions 74 or 76 of the backing substrate 52 and is preferably free of fastening adhesive 54. This reduces the amount of fastening adhesive used and ensures that the fastening adhesive does not interfere with the bonding of the fixed end 77 to the absorbent article.

The fixed end 77 of the tape tab 40 is preferably bonded to a surface of the absorbent article by a permanent bond. The permanent bond may be formed by any means known in the art, including, but not limited to ultrasonic bonding, autogenous bonding, friction bonding, heat bonding, pressure bonding, heat and pressure bonding or adhesive bonding. (As used herein, the terms "permanent", "permanently joined" or "permanent bond" refer to bonds or means for bonding one element with another element, wherein the bond between the elements is meant to be relatively strong such that the elements will not generally become unjoined during normal use of the product.) Although any bonding means known in the art may be used, it is preferred that the bond be a mechanical bond so as to create a surface that acts as a release surface 79 for the fastening adhesive 54 disposed on the releasable end 78 of the tape tab 40. (The area of the release surface 79 is preferably as large, or larger than the area of the releasable end 78 tape tab 40 comprising fastening adhesive 54.) The release surface 79 provided by the bonded area permits the releasable end 78 of the one-piece tape tab 40 to be releasably stored without the use of any added release agent or substrate.

The bonded area of the fixed end 77 need only be large enough to ensure that the tape tab 40 will be securely fixed to the absorbent article once the mechanical bonding process is complete. The fixed end 77 of the tape tab 40 may be joined to the topsheet 22 or the backsheet 24 of the absorbent article. Further, the fixed end may be joined between the topsheet 24 and the backsheet 26, or to any other element of the absorbent article. One preferred embodiment is shown in FIG. 12, wherein the fixed end 77 of the tape tab 40 is joined to the topsheet 24 of the absorbent article.

In an especially preferred embodiment, as shown in FIG. 12, at least a portion of the ear flap 30 in the vicinity of the fixed end 77 of the tape tab 40 is mechanically manipulated to provide the release surface 79. (As used herein, the term "mechanical manipulation" refers to the process of changing the physical attributes of a substance by means including, but not limited to, heat, pressure, heat and pressure, friction, ultrasonics or embossing.) This may reduce the amount of the tape tab 40 needed for the fixed end 77, reducing the cost of the tape tab and thus, the cost of the absorbent article. In such embodiments, the fixed ends 77 of the tape tabs 40 may be joined to the absorbent article by the means used to create the mechanically manipulated region of the ear flap 30, or by means other than those used in the mechanical manipulation. Thus, the fixed end 77 may be joined to the ear flap 30 by any means known in the art, including those described herein, such as adhesives. One adhesive suitable for bonding the fixed end 77 of the tape tab 40 is the hot melt adhesive HL-1358 manufactured by the H. B. Fuller Company of St. Paul, Minn.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a front waist region, a rear waist region and a crotch region located there between, the absorbent article comprising:

a chassis having a pair of opposed longitudinal edges, said chassis including a liquid permeable topsheet, a liquid impermeable backsheet joined with said topsheet and an absorbent core disposed between said topsheet and said backsheet;

an ear flap extending laterally outwardly from one of said longitudinal edges in at least said rear waist region, said ear flap having a garment facing side and a body facing side, only a portion of said body facing side of said ear flap being embossed, said embossed portion of said body facing side of said ear flap forming a release surface; and a tape tab having a fixed end and a releasable end, said fixed end being joined to said ear flap adjacent said embossed portion of said ear flap such that said releasable end of said tape tab may be releasably joined to said embossed portion of said body facing side of said ear flap.

2. The absorbent article of claim 1 wherein said fixed end of said tape tab is bonded to said ear flap by a mechanical bond selected from the following group: heat bonding, pressure bonding, heat and pressure bonding, ultrasonic bonding, friction bonding, or autogenous bonding.

3. The absorbent article of claim 1 wherein said fixed end is bonded to said topsheet, said backsheet or between said topsheet and said backsheet of said absorbent article.

4. The absorbent article of claim 1 wherein said fixed end of each of said tape tabs is joined to said absorbent article by an adhesive.

5. The absorbent article of claim 1 wherein said releasable end of said tape tab comprises an adhesive selected from the following group: pressure-sensitive adhesive, cohesive, water based adhesive, solvent based adhesive.

6. The absorbent article of claim 1 comprising an ear flap extending outwardly from each of said opposing longitudinal edges and a tape tab joined to each of said ear flaps.

7. The absorbent article of claim 1 wherein said fixed end of each of said tape tabs is joined to said absorbent article by said mechanical bond and an adhesive.

8. A disposable article to be worn about a wearer's torso having a front waist region, a rear waist region and a crotch region located therebetween, the disposable article comprising:

a chassis having a pair of opposed longitudinal edges, said chassis including a liquid permeable topsheet and a liquid impermeable backsheet joined with said topsheet;

an ear flap extending laterally outwardly from one of said longitudinal edges in at least said rear waist region, said ear flap having a garment facing side and a body facing side, only a portion of said body facing side of said ear flap being embossed, said embossed portion of said body facing side of said ear flap forming a release surface; and a tape tab having a fixed end and a releasable end, said fixed end being joined to said ear flap adjacent said embossed portion of said ear flap such that said releasable end of said tape tab may be releasably joined to said embossed portion of said body facing side of said ear flap.

9. The disposable article of claim 8 wherein said fixed end of said tape tab is bonded to said ear flap by a mechanical bond selected from the following group: heat bonding, pressure bonding, heat and pressure bonding, ultrasonic bonding, friction bonding, or autogenous bonding.

10. The disposable article of claim 8 wherein said fixed end is bonded to said topsheet, said backsheet or between said topsheet and said backsheet of said absorbent article.

11. The disposable article of claim 8 wherein said fixed end of each of said tape tabs is joined to said absorbent article by an adhesive.

12. The disposable article of claim 8 wherein said releasable end of said tape tab comprises an adhesive selected from the following group: pressure-sensitive adhesive, cohesive, water based adhesive, solvent based adhesive.

13. The disposable article of claim 8 comprising an ear flap extending outwardly from each of said opposing longitudinal edges and a tape tab joined to each of said ear flaps.

* * * * *